United States Patent [19]
Romaine

[11] Patent Number: 5,123,907
[45] Date of Patent: Jun. 23, 1992

[54] APPLIANCE FOR USE IN EXCISING SKIN FROM STRETCHED SKIN, AND METHOD

[76] Inventor: Richard A. Romaine, 475 SW. View Crest Dr., Gresham, Oreg. 97080

[21] Appl. No.: 716,295

[22] Filed: Jun. 17, 1991

[51] Int. Cl.⁵ .............................................. A61B 17/00
[52] U.S. Cl. .................................. 606/131; 604/115; 604/116
[58] Field of Search .................. 604/115, 116, 117; 128/749, 751, 754, 662.05, 630, 897, 898; 132/319; 606/131, 184, 167

[56] References Cited

U.S. PATENT DOCUMENTS

| | | | |
|---|---|---|---|
| 2,238,323 | 4/1941 | Hollingsworth | 604/117 |
| 3,522,800 | 8/1970 | Lesser | 128/20 |
| 3,807,405 | 4/1974 | Niebel | 606/131 |
| 4,177,802 | 12/1979 | Ogami | 128/20 |
| 4,542,742 | 9/1985 | Winkelman et al. | 606/167 |
| 4,832,045 | 5/1989 | Goldberger | 128/754 |
| 4,883,053 | 11/1989 | Simon | 604/116 X |
| 4,936,325 | 6/1990 | Davis | 132/319 |
| 4,981,142 | 1/1991 | Dachman | 128/749 |

FOREIGN PATENT DOCUMENTS 2584601  1/1987  France .................. 128/754

*Primary Examiner*—John J. Wilson
*Assistant Examiner*—Jeffrey A. Smith
*Attorney, Agent, or Firm*—Eugene D. Farley

[57] ABSTRACT

An appliance for use in excising skin samples from stretched skin, as in taking punch biopsies. The appliance comprises a piece of material having a transverse central opening dimensioned to clear the sample-incising tool. It also has a skid-resistant, skin-contacting surface and an opposite pressure-applying surface. It is adapted for placement on a stretched skin area with its skid-resistant surface in pressure contact with the stretched skin and its pressure applying surface positioned for the application of digital pressure as required to maintain the skin in stretched condition during the sample-incising operation.

The appliance preferably is used with the skin stretched in a direction perpendicular to the skin Langer's lines, thereby producing a skin defect which is elliptical in contour and effectively sutured.

6 Claims, 1 Drawing Sheet

APPLIANCE FOR USE IN EXCISING SKIN FROM STRETCHED SKIN, AND METHOD

This invention relates to an appliance for use in excising skin samples from stretched skin. It pertains particularly to an appliance for use in excising skin samples for use in biopsy procedures and is described herein with particular reference to that use, although no limitation thereby is intended. For example, it also may be used in the excision of skin lesions such as moles, fibromas and the like.

The invention relates further to a novel method for excising skin samples.

BACKGROUND AND GENERAL STATEMENT OF THE INVENTION

In the practice of medicine, it frequently is necessary to excise a skin sample from a given skin area. An example of such a procedure is the excising of skin samples in the performance of biopsies.

As is well known, a biopsy is a surgical procedure performed on the skin or other organ to sample tissue structure and cell content, usually to assist in disease diagnosis.

A skin biopsy may be accomplished in different ways. For instance, a scalpel blade may be used to cut into the skin and excise samples of various sizes. This procedure almost always requires suturing the wound edges together.

In the alternative, the biopsy sample may be obtained by slicing or shaving the skin horizontally to remove an elevated portion. This procedure usually does not require suturing.

The method of sampling skin tissue most often used by dermatologists relies upon the use of an instrument called a skin punch. This is a short, pencil-shaped tool having one end in the form of an open cylinder provided with a sharp, cutting blade. The punch is held at its upper, solid end by the thumb and one or two fingers and twirled while it rests on and is pressed lightly into the skin surface. This creates a plug of tissue which can be snipped loose from its underlying attachment and submitted to the laboratory for examination.

The punch biopsy routine may or may not require suturing. If the defect is only 1–3 mm in diameter, natural and unassisted healing usually will be adequate. However, if the defect is larger, suturing will hasten the healing. It also will result in the formation of a less conspicuous scar.

Although widely used, the foregoing procedure has a significant disadvantage. The biopsy punch inherently cuts a circular opening in the skin. When the edges of a circular opening are brought together, the distal portions splay out and pucker to form nipple-like protrusions. The resulting scar is unsightly and cosmetically undesirable.

To overcome this problem, a procedure has been developed which takes advantage of the fact that there exist in the skin variously disposed lines of natural skin tension. These are called "Langer's lines". They may be taken advantage of to create in the skin an elliptical opening rather than a circular one. The elliptical opening is readily amenable to effective suturing procedures.

Accordingly, to carry out the skin sampling procedure a lateral stretching force is applied to the skin in the skin sampling area. This force is applied in the direction perpendicular to the lines of greater tension.

The stretched skin then is incised to make a substantially round cut defining the sample. The stretching force is removed and the sample excised by cutting or snipping it away from the anchoring tissue.

As this is done, the opening in the skin, which originally is circular, becomes elliptical. This is owing to deformation by the lines of tension (Langer's lines) which exist in the skin. As noted, the elliptical opening may be sutured effectively.

However, even this improved technique is characterized by a problem the solution to which is the object of the present invention.

In carrying out a punch biopsy, the surgeon normally stretches the skin in the biopsy area by applying stretching force perpendicular to Langer's lines with the thumb and forefinger of one hand while manipulating the biopsy punch with the other hand. It is the surgeon's intention to maintain the stretching tension for the entire duration of the sampling procedure.

In practice, this may be difficult to do.

First, because of inattention, distraction, fatigue, absorption in his work or other disturbing factors, the surgeon at the critical moment of taking the biopsy sample may relax the skin-stretching pressure or his fingers may slip. As a result, the punched out opening ("defect") in the skin assumes a round configuration rather than the desired elliptical configuration.

Secondly, the surgeon for any of the above reasons may apply the stretching force in a direction other than the desired direction precisely perpendicular to Langer's lines. In either case, the result is the same. The desired elliptical skin opening is not obtained.

It is the primary object of the present invention to provide an appliance for use by an operator performing the above described skin sampling procedure which will maintain the desired lateral pressure and orientation in the skin sampling area even if the finger pressure and/or direction of force are altered. The device is simple in construction, inexpensive, and easily used. It makes foolproof an important procedure which formerly was susceptible to inaccurate performance.

Broadly stated, the skin sample excising appliance of my invention comprises a thin, fairly rigid, flat or slightly convex rectangular or circular body with a center hole. The inferior surface necessarily, and the superior surface preferably, are processed to make them skid resistant when pressure is applied.

To use the appliance, lateral pressure is exerted perpendicular to Langer's lines by the fingers of the hand which later will hold and use the skin incising tool, e.g. the biopsy punch. The appliance is placed between the laterally pressing fingers which establish the intended, ideal orientation and magnitude of pressure.

It then is held down and in place by the non-biopsying hand, thus holding the underlying stretched skin in its desired optimum stretched condition while the skin sample is incised.

If the surgeon's fingers twist or relax, there will result no change in the surgery field, tension or orientation because the appliance by friction will keep the skin stretched, as it was at the time of appliance placement. The desired easily and effectively sutured elliptical opening in the skin accordingly is obtained.

THE DRAWINGS

DESCRIPTION OF PREFERRED EMBODIMENTS OF THE INVENTION

Figure 3:
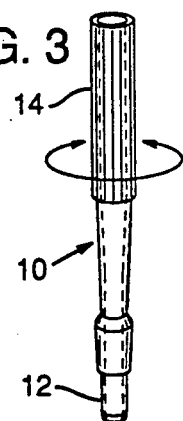
FIG. 3 is a top perspective view of a conventional skin biopsy punch of the class with which the herein described appliance may be used.

As indicated above, the herein described appliance for use in obtaining skin samples from stretched skin is adapted for use particularly with a biopsy punch such as is illustrated in FIG. 3.

The punch 10 comprises a cylindrical cutter 12 on the end of a shaft 14 which preferably has a knurled segment for positive gripping by the operator.

In use, the punch is placed against the tissue area to be sampled and twirled back and forth with the fingers as indicated in FIG. 3. As this is done, pressure transmitted to the cutting edge of the punch carries it downwardly, incising the tissue to the desired depth and producing a cut defining the sample. The punch then is withdrawn. Upon withdrawal of the punch, the sample is excised with a scissors or other suitable cutting tool.

Figure 7:
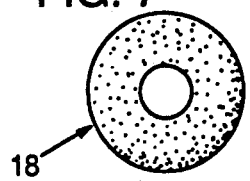
FIGS. 7, 8 and 9 are schematic plan views illustrating various contours which may be assumed by the appliance.
Figure 8:
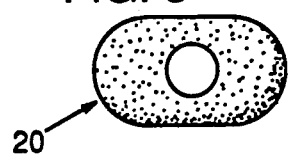
Figure 9:
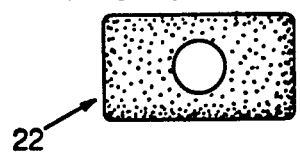

The appliance of my invention which is used in combination with a punch of the character described is indicated generally at 16. It comprises a sheet or block of size and contour appropriate for its intended application. Its contour may be round, elliptical, or rectangular as shown in the embodiments indicated at 18, 20 and 22, respectively, of FIGS. 7, 8 and 9.

The sheet or block may be made of any suitable material. It preferably comprises a disc of stiff plastic or pliable metal. The disc is made of a stable, heat and corrosion resistant substance so that it can be sterilized. There should be enough surface to grip the underlying skin and to offer frictional resistance to the pressing fingers. For effective contact, the disc preferably is slightly concave relative to the underlying skin.

The appliance has a central hole 24 sized to receive punch 10. The opening should be sufficiently large to expose around the punch a border of skin of sufficient extent to orient the surgeon properly as he places the punch.

Appliance 16 has an undersurface 26 and an upper surface 28. Both surfaces are skid resistant: the undersurface in order to maintain the appliance properly in position during the excising operation, and the upper surface to insure that the surgeon's fingers will not slip.

The skid resistant surface may be achieved in a desired manner, as for example by coating the surfaces with a tacky material, or by roughening the surfaces to make them grainy or gritty.

Figure 2:
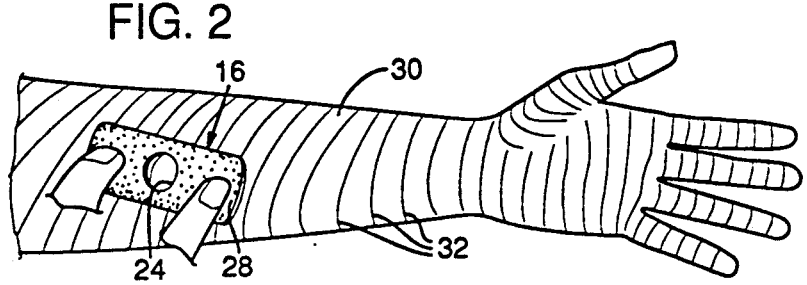
FIG. 2 is a top perspective view of the ventral forearm and palm illustrating the appliance placed thereon in position for incising the skin sample.
Figure 1:
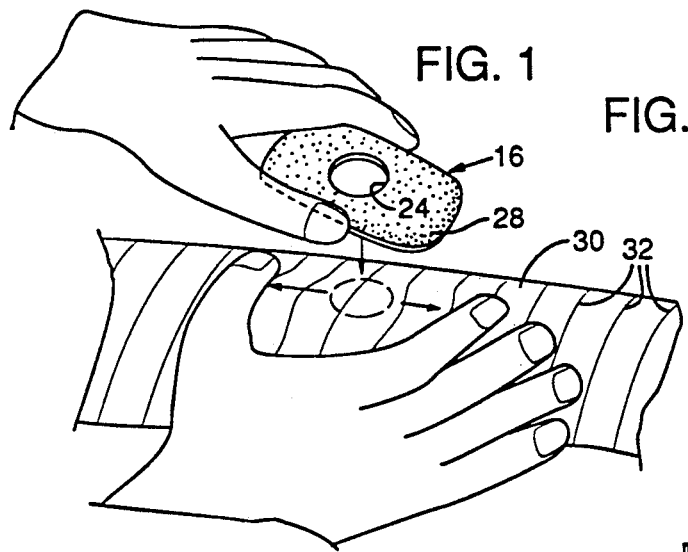
FIG. 1 is a top perspective view including a section of the ventral forearm with the Langer's lines illustrated thereon, depicting the manner of placement of the herein described appliance.

The manner of using the appliance in conjunction with the biopsy punch is illustrated particularly in FIGS. 1 and 2.

In the illustrated situation, the sample to be taken is a sample of skin from the ventral forearm 30. As illustrated schematically in the drawings, and as discussed hereinabove, the skin in this area of the body is characterized by the presence of Langer's lines or tension lines 32. These circle the arm roughly parallel to each other in the indicated manner.

In carrying out the procedure, the surgeon first with one hand stretches the skin in a direction perpendicular to Langer's lines. As illustrated in FIG. 1 the stretching is accomplished by exerting lateral pressure using the fingers of the hand which later will hold and use the biopsy punch.

The appliance is placed between these laterally pressing fingers. It then is held down and in place in its ideal orientation using the correct amount of pressure by the fingers of the non-biopsying hand. It now holds the underlying skin in the desired position and orientation, as illustrated in FIG. 2.

Figure 4:
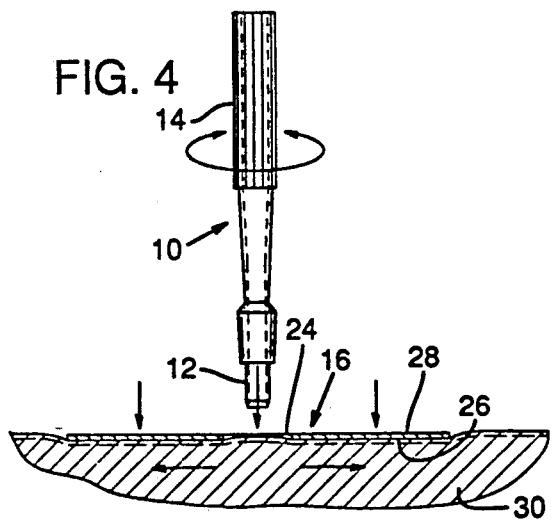
FIGS. 4 and 5 are views in elevation, partly in section, illustrating the manner of use of the appliance of my invention with the punch of FIG. 3.
Figure 5:
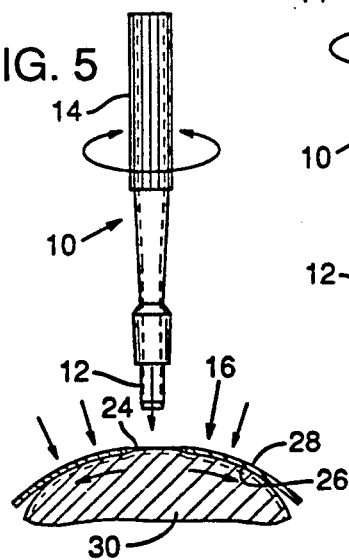

While holding the appliance in position with one hand, the surgeon grasps the biopsy punch with his operating hand; locates it centrally of opening 24 in the appliance; and with the twirling motion illustrated in FIGS. 4 and 5 incises the skin. During this operation he maintains digital pressure on the upper surface 28 of the appliance. This prevents his fingers from slipping.

At the same time, the skid resistant undersurface 26 of the appliance firmly engages the skin so that the appliance itself will not slip and change its orientation. This condition obtains even if the surgeon's stabilizing fingers inadvertently should twist or relax their pressure. In that event, there will be no change in the surgery field tension or orientation because the appliance by friction will keep the skin stretched as it was at the time of appliance placement.

Figure 6:
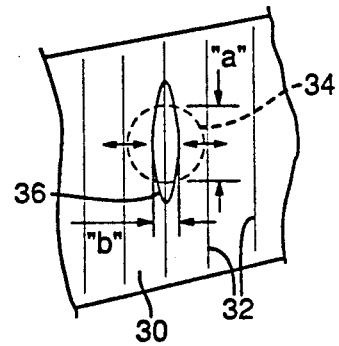
FIG. 6 is a diagrammatic view illustrating the manner in which the punch-appliance combination produces an elliptical opening in the skin following the skin-sampling procedure.

In this manner it is insured that the stretching pressure will be exerted continuously in the direction normal to the Langer's lines so that the desired result illustrated in FIG. 6 is obtained.

As shown in that figure, the punch cuts a circular opening 34 indicated in dashed lines and having a dimension "a". However, because of the tension forces present in the skin, upon removal of the punch and skin sample and release of the lateral pressure on the skin, the opening in the skin assumes the elliptical shape 36. This has the dimension "b", ideal for suturing.

Having thus described in detail a preferred embodiment of the present invention, it will be apparent to those skilled in the art that many physical changes may be made in the apparatus without altering the inventive concepts and principles embodied therein. The present embodiment is therefore to be considered in all respects as illustrative and not restrictive, the scope of the invention being indicated by the appended claims.

I claim:

1. A method of excising skin samples which comprises:
    a) stretching the skin in a sample area in a direction substantially perpendicular to the direction of the skin Langer's lines,
    b) providing an appliance comprising a sheet or block having a transverse opening dimensioned to clear a skin incising tool during the skin sampling procedure,
    c) the appliance having a skid-resistant, skin-contacting surface and an opposite pressure-applying surface, d) placing the appliance on the stretched skin with the skid-resistant surface in pressure contact with the skin and with the pressure-applying surface positioned for the application of external pressure as required to maintain the skin beneath the appliance in stretched condition during the sample incising operation, e) incising the stretched skin to make a substantially round cut defining the sample, f) removing the appliance from the stretched skin area, thereby permitting the tension forces of the skin to alter the round configuration of the hole to an elongated, substantially elliptical configuration, and g) excising the sample.

2. The method of claim 1 including the step of suturing the resulting elongated skin defect.

3. The method of claim 1 wherein the skin sample comprises a biopsy skin sample and wherein the stretched skin is incised by a biopsy punch.

4. The combination of a biopsy punch and a stretched skin excising appliance comprising
   a) a sheet or block having a transverse opening dimensioned to clear the skin biopsy punch,
   b) the appliance having a skid-resistant, skin-contacting surface coated with a tacky material and an opposite pressure-applying surface,
   c) the appliance being adapted for placement on a stretched skin area with the skid-resistant surface in pressure contact with said area and the pressure-applying surface positioned for the application of external pressure as required to maintain the skin beneath the appliance in stretched condition during the sample-excising operation.

5. The appliance of claim 4 wherein the pressure applying surface comprises a frictional surface.

6. The appliance of claim 4 wherein the skin-contacting surface has a concave configuration.

* * * * *